US005136032A

United States Patent [19]

Nagamatsu et al.

[11] Patent Number: 5,136,032

[45] Date of Patent: Aug. 4, 1992

[54] METHOD FOR SEPARATING PHOSPHOPOLYOL COMPOUNDS USING A SEPARATING AGENT

[75] Inventors: Shinji Nagamatsu; Yoshikazu Tanaka; Thoru Shibata, all of Hyogo, Japan

[73] Assignees: Daicel Chemical Industries, Ltd., Sakai; Tanabe Seiyaku Co., Ltd., Osaka, both of Japan

[21] Appl. No.: 619,937

[22] Filed: Nov. 29, 1990

[30] Foreign Application Priority Data

Dec. 7, 1989 [JP] Japan ................................. 1-320141

[51] Int. Cl.[5] ........................ B01D 13/00; C08C 8/00; C07H 5/00

[52] U.S. Cl. .................................... 536/187; 536/4.1; 536/123; 210/651; 210/654; 210/500.38; 210/500.37; 514/119

[58] Field of Search ....................... 536/18.7, 4.1, 122, 536/123; 530/415, 345, 812; 435/181; 424/88; 210/651, 654, 500.38, 500.37; 514/119

[56] References Cited

U.S. PATENT DOCUMENTS

| | | | |
|---|---|---|---|
| 4,261,834 | 4/1981 | deWinter | 210/651 |
| 4,696,980 | 9/1987 | Porath | 536/18.7 |
| 4,759,850 | 7/1988 | Farnand et al. | 210/654 |
| 4,788,182 | 11/1988 | Baschang et al. | 514/119 |
| 4,909,942 | 3/1990 | Sato et al. | 210/651 |
| 4,915,839 | 4/1990 | Marinaccio et al. | 210/500.38 |
| 4,963,664 | 10/1990 | Yalpani et al. | 536/18.7 |

*Primary Examiner*—Ronald W. Griffin
*Assistant Examiner*—Louise Leary
*Attorney, Agent, or Firm*—Flynn, Thiel, Boutell & Tanis

[57] ABSTRACT

A phosphopolyol compound, such as pyrogens, is separated from a solution to be used in the pharmaceutical field by bringing the solution into contact with a porous adsorbent which has a pore size of 1 nm to 20 microns and comprises a base material and a functional chain group of an aliphatic amine having a chain length of 2 to 50, bonded to the base material.

18 Claims, No Drawings

METHOD FOR SEPARATING PHOSPHOPOLYOL COMPOUNDS USING A SEPARATING AGENT

The invention relates to a method for the separation of phosphopolyol substances (PPS), such as toxic pyrogens from a liquid to be introduced directly into a living body, such as an injection, a dialysing fluid and an infusion and then also to a diluting water and a washing water in the field. The method of the invention may be applied to an organic solution for the same purpose. It can adsorb DNA and RNA in the field of gene technology. It is useful for adsorption of PPS from bacterium and animal cells.

PPS is defined as a compound composed of a phosphoric acid moiety and a polyol moiety, such as LPS (lipopolysaccharide), lipid A, nucleic acid and a glycerol phosphate compound. Many such polyol compounds have physiological activity. They, even when present in a small amount, can be removed by the invention.

The invention relates moreover to an agent for separating PPS from a liquid.

PRIOR ART

An adsorbent is used for the purpose of separating substances contained in a liquid. The relative difficulty of separation techniques used in the industry varies depending upon various factors, such as the kinds of substances contained in the system, separating power and throughput. Removal of a pyrogen is an example of a separation technique wherein the severity of requirements is especially high. Examples of the technical field similar thereto include removal of a nucleic acid and other PPS.

Examples of the liquid from which a pyrogen should be removed include liquids directly introduced into a living body without passing through a digestive tract, such as liquid medicines for injection, nutrient infusion, and dialysis, as well as diluent water for these medicines; apparatuses for handling the above-described liquids; and wash water for containers of the above-described liquids.

A pyrogen is a substance that produces an abnormal increase in the body temperature of homotherms, even in very small amounts. When the pyrogen enters into blood as a contaminant of an intravenous injection, etc., there occurs a severe fever independently of the effect of the drug. It is believed that when the above-described action is excessive, there occurs a fever attended with a shaking chill and, in some cases, shock death. Bacterial substances, inflammatory substances, vegetable polysaccharides, blood group substances or the like are known as pyrogens. Among them, bacterial substances are most deeply involved in causing fevers and are called a bacterial toxin, which is broadly classified into an exotoxin and an endotoxin. Among the above-described toxins, the endotoxin known as the so-called O antigen which is composed mainly of a cell wall lipopolysaccharide (LSP) of Gram-negative bacteria, has the strongest pyrogenic property and cannot be deactivated, even by heat treatment. Once the endotoxin is incorporated into a liquid by chance, it is very difficult to remove. Thus, the term pyrogens applies equally to endotoxins or LPS.

Chemical decomposition, membrane separation, gel filtration, adsorption, etc. are known as methods of removing a pyrogen. The applicability of chemical decomposition is limited due to the resistance of a substance to be treated to a decomposer, problems derived from contamination with a decomposer and a decomposition product, etc.

Membrane separation and gel filtration can be regarded as separation methods wherein a difference in the size between the pyrogen and the substance to be treated is utilized. Regarding the size of the pyrogens, and the variety of pyrogens, the association of LPS and the presence of lipid A should also be taken into account. Specifically, even when the pyrogen is limited to LPS, which is the most important substance among various pyrogens, an aliphatic chain of the portion involved in the pyrogenic action, i.e., lipid A, and a polysaccharide bonded thereto are each specific and vary according to the type of bacteria as an origin of LPS. An LPS having a molecular weight of about 5000 associates to form a large micellar structure having a molecular weight as large as several millions, while lipid A, having a molecular weight of about 2000 per se, is a pyrogen.

An ultrafiltration membrane (UF membrane) and a reverse osmosis membrane (RO membrane) are used for the removal of a pyrogen by means of a membrane. An apparatus comprising a plurality of membranes has also been proposed for the purpose of attaining a low pyrogen content for the pyrogen removing technique which use membranes. Examples thereof include apparatuses disclosed in Japanese Patent Laid-Open No. 207517/1982 and U.S. Pat. No. 4261834 (by de Winter). When the liquid to be treated is an aqueous solution consisting of water and a low molecular weight drug, a separating membrane permeable to the substance to be treated and impermeable to a pyrogen and a pyrogen-containing cell may be selected for use. However, when the molecular weight of the substance to be treated is large, it is not easy to select a membrane which permits the substance to be treated to permeate therethrough in a good recovery while inhibiting the permeation of a pyrogen, particularly one having a low molecular weight as well, to attain an intended low pyrogen concentration.

In the case of the administration to a rabbit a dose of 10 ml/kg at a calorific value of 5 EU (endotoxin unit)/kg at a titer of 10 EU/ng, for example, the target concentration is 0.5 EU/ml or 50 pg/ml or below.

It is more difficult to select a membrane which can be successfully used in the removal of a pyrogen from a liquid containing a high molecular weight substance, such as protein, which makes it almost impossible to remove the pyrogen to a satisfactory low level while maintaining a high drug recovery. In general, separation of substances whose molecular weights lie close together cannot be attained through membrane filtration, which renders membranes unsuitable for use in the removal of a substance having a broad molecular weight distribution, such as a pyrogen.

It is known that activated carbon and ion exchange resins have the capability of adsorbing and removing a pyrogen. Further, a material for a porous separating membrane, e.g., a polyolefin, as well has a capability of adsorbing a pyrogen through a hydrophobic bonding force. However, the above-described materials cannot selectively adsorb a pyrogen from a drug-containing liquid to a very low pyrogen concentration and, therefore, are unsatisfactory as an adsorbent used in obtaining a drug solution from which the pyrogen has been sufficiently removed.

Other materials having the capability of adsorbing a pyrogen are also known. For example, Japanese Patent Laid-Open No. 112888/1984 discloses a method of removing Gram-negative bacteria and cell wall components thereof by means of an amino group-containing fiber. It may be understood that the lowest pyrogen concentration attained in the working examples described in the above-described laid-open specification is 0.014 mg/ml, i.e., 14000 ng (nanogram), with a percentage removal of 86% obtained in the treatment of an aqueous solution containing 0.1 mg/ml of a lipopolysaccharide.

In U.S. Pat. No. 4,639,513 (Houe et al.), ion chromatography used in removing macromolecular proteins was used as a means for purifying IgG (a plasma component), while affinity chromatography was used for removing enzymes. This patent further describes the removal of pyrogens and suggests that LPS may be removed by using a positively charged ion exchange matrix. Although this patent is silent about the structure of the positively charged ion exchange matrix in the description on the removal of pyrogens, the foregoing description on the ion exchange chromatography suggests that it may be a graft copolymer such as cellulose-GMA-DEAEMA (diethylaminoethyl methacrylate). Furthermore, a material obtained by aminating a cellulose-GMA matrix (refer to FIG. 9 of said patent) with ethylenediamine is disclosed as a fixed bed for chromatography having a similar structure in the description, not for the removal of the LPS, but for affinity chromatography therein.

U.S. Pat. No. 4,663,163 (Houe et al.) describes a substance wherein a synthetic polymer, which is obtained by radical-copolymerizing a monomer having an epoxy group and a vinyl group with an aminoalkyl ester of an unsaturated acid, is bonded to a polysaccharide via a covalent bond. It seems that this substance, which is used as a carrier in chromatography, is essentially the same as the cellulose-GMA-DEAEMA graft copolymer described in the U.S. Pat. No. 4,639,513.

U.S. Pat. No. 4 491 660 to Gendrich et al. discloses a matrix comprising an insoluble polymer, an alkyl group and a cyclic compound of the benzene type with an isourea group or an amide binding group, being capable of being attached to endotoxin. The matrix of the reference comprises a cyclic compound of the benzene type substituted by a nitrogen-containing functional group such as amino groups and amidino groups, though it seems that it can hydrophobically bond to pyrogens.

In recent years, an affinity adsorbent capable of specifically adsorbing a pyrogen and, therefore, useful for the removal of a pyrogen incorporated in a drug-containing liquid has become commercially available. Representative examples of this type of adsorbent include polysaccharide gels having a nitrogen-containing cyclic compound bonded thereto as disclosed in the Japanese Patent Laid-Open No. 183712/1982. These gels are highly appreciated in the art because they have a capability of selectively adsorbing and removing a pyrogen having various and broad ranges of molecular weights from an aqueous solution containing a high molecular weight drug such as protein. The pyrogen concentration described in the above-described laid-open specification reaches 0.1 ng (nanogram)/ml (0.5 EU/ml) or less.

A pyrogen adsorbent is further required to be capable of treating a solution having a high ionic strength. In ion exchange chromatography the elution power is elevated with an increase in the ionic strength of an eluent. In adsorption, wherein an ionic bond participates, as is apparent from the above fact, the adsorption force tends to be generally reduced as the ionic strength of a solution increases. Thus the ability to remove pyrogens of the above-mentioned pyrogen adsorbent bonded to a nitrogen-containing cyclic compound is reduced with an increase in the ionic strength of a drug solution (see Biotech. Appl. Biochem., 10, 147). Accordingly, the efficient removal of pyrogens from a solution of a high ionic strength would lead to a new possibility of the treatment of drug solutions of high concentrations.

It has been known that an antibiotic, polymyxin, can inactivate pyrogens. However this substance exerts a serious side effect (renal toxicity), which restricts the application thereof in a living body. In order to overcome this problem, Japanese Patent Publication No. 16389/1989 proposes a pyrogen adsorbent wherein polymyxin is immobilized on an insoluble carrier.

It is an object of the present invention to provide an adsorption separating agent having a high safety which is excellent in its ability to remove phosphopolyol compounds such as pyrogens from a solution having a high ionic strength and withstands a pressure at a high flow rate. No technique for achieving the above-mentioned object has been known hitherto.

SUMMARY OF THE INVENTION

The invention provides a method for separating a phosphopolyol compound from its solution, comprising the steps of bringing the solution into contact with a porous adsorbent which has a pore size of 1 nm to 20 microns and comprises a base material and a functional chain group of an aliphatic amine type having a chain length of 2 to 50, bonded to the base material.

The functional group will serve in the adsorption and eventual separation of the phosphopolyol. The functional effect will be due to amino groups contained in the functional group.

It is more advantageously effective that the phosphopolyol is a pyrogen and the solution is an aqueous solution of a drug or medicine having an ionic strength of from 0.03 to 0.5 micron.

According to an alternative method of the invention, the phosphopolyol and a drug or medicine are adsorbed on the adsorbent and then the adsorbent is brought into contact with an aqueous solution having a high ionic strength to thereby elute the drug or medicine selectively.

In the methods of the invention, the adsorbent or separating agent may be in the form of a microfiltration membrane or an ultrafiltration membrane. Alternatively, the adsorbent may be in the form of hard gel beads, preferably having a pore size of 10 nm to 5 microns.

The invention further provides a separating agent comprising a base material and a functional chain group having a chain length of 2 to 50, bonded to the base material, the group being an aliphatic, primary or secondary amine group, and having a pore size of 1 nm to 20 microns.

The separating agent may be in the form of a microfiltration membrane or an ultrafiltration membrane or in the form of hard gel beads, preferably having a pore size of 10 nm to 5 microns.

It is preferable that the functional chain group is a primary or secondary aliphatic amine group. It is preferable that the base material is a polyhydroxyl polymer having a pore size of 50 nm to 1 micron.

It is preferable that the functional chain group has a diaminoalkylene moiety of 1 to 12 carbon atoms.

In a preferable embodiment of the separating agent, the base material is a polysaccharide or a polyvinyl alcohol polymer and has as an intermediate group of the functional chain, a hydroxy-substituted propylene bonded to an oxygen atom of the base material.

It is preferable that the functional chain group includes an amino acid residue bonded to the diaminoalkylene moiety.

In another preferable embodiment of the agent, the base material is selected from the group consisting of a polysaccharide and a polymer of vinyl alcohol, the functional chain group includes a hydroxypropylene group bonded at its one end to an oxygen atom contained in the base material and the functional chain group is an aliphatic amine group having a chain length of 2 to 50. The functional group preferably has a chain length of 3 to 35 and includes therein 1 to 5 nitrogen atoms.

In a different preferable embodiment of the separating agent, the base material is a porous polysaccharide and the functional group has the following formula:

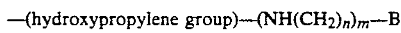

—(hydroxypropylene group)—$(NH(CH_2)_n)_m$—B in which n is a number of 1 to 12, m is zero or one and B is guanidino or a natural polyamine.

It is more preferable that the base material is a porous cellulose and the functional group has the following formula:

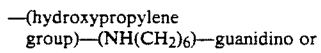

—(hydroxypropylene group)—$(NH(CH_2)_6)$—guanidino or

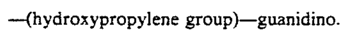

—(hydroxypropylene group)—guanidino.

In the case, a preferably functional group has the following formula:

—(CH2—CH(OH)—CH2)—$(NH(CH_2)_n)_m$—B in which n is a number of 1 to 12, m is zero or one and B is guanidino or a natural polyamine.

The above-mentioned object can be achieved in the following manner. Namely, the present invention provides a separation method comprising contacting a solution containing a phosphopolyol compound with a porous adsorbent having an aliphatic amine group for the functional group, having a chain length of 2 to 50, being bonded to a base material, the adsorbent having a pore size of 1 nm to 20 microns. The functional group preferably includes a primary amine group or a secondary amine group.

Furthermore, the present invention provides a separating agent for adsorbing a phosphopolyol compound in the form of a porous adsorption separating agent comprising a base material and a functional chain bonded thereto and having a pore size of from 1 nm to 20 microns, said functional chain being a primary amine group or a secondary amine group.

Typical examples of the phosphopolyol compound solution to which the present invention is to be applied are aqueous drug solutions containing pyrogens and having an ionic strength of from 0.03 to 0.5, in particular, those having an ionic strength similar to that of physiological saline. However, the present invention may be applied to solutions over a wider ionic strength ($\mu$) range, for example, from 0 to 5. Further, the present invention is applicable to a low ionic strength region (for example, nonionic drug solutions) wherein conventional adsorbents containing nitrogen-containing cyclic compounds are highly available.

The separating agent comprises a porous base material and an aliphatic amine group having a chain length of 2 to 50, bonded to the base material. The functional group consisting of the aliphatic amine group is distinct from a heterocyclic chain, an aromatic amine chain and a peptide chain. The base material is distinct from other fiber and beads in view of its pore size. The functional group is limited in respect to the chain length and is not polymeric to a substantial extent. The nitrogen-basic group is bonded to an aliphatic carbon only. The functional group is substantially a chain-like group and is not a group comprising a cyclic structure in the main body from the viewpoint of the nitrogen, such as a nitrogen-containing heterocyclic group and an aromatic amine group.

The porous base material preferably include polyhydroxyl polymers. A reactive moiety such as a hydroxyl group is useful in binding the functional chain to the base material. For example, a functional chain which has a hydroxyl-substituted propylene intermediate chain directly bonded to an oxygen atom of the base material and a diaminoalkylene moiety may be obtained by reacting epichlorohydrin with a hydroxyl group of the base material and further reacting an alkylenediamine therewith. The aliphatic nitrogen atom of the functional chain may be further bonded to an amino acid residue.

A typical characteristic of the present invention resides in that a phosphopolyol compound can be selectively adsorbed from a solution having an ionic strength similar to that of physiological saline (for example, from 0.07 to 0.3). The term "selectively" as used herein means that pyrogens can be substantially removed in the presence of a drug having an acidic group such as a protein and the drug can be recovered at a high yield. The separating agent of the present invention can exert its selective adsorption effect over a wide range of pH values. For example, it is available in a pH range of from 3 to 11, at an ionic strength of 0.1.

Typical examples of the phosphopolyol compound to be removed in the present invention are pyrogens which will be, therefore, mainly mentioned hereinafter.

The separating agent of the present invention is usually employed as an adsorption/retention separating agent and differs from chromatographic techniques used in some of the cited references of the prior arts.

A typical example of the porous adsorbent is a hard gel bead having a pore size of from 10 nm to 5 $\mu m$, preferably from 50 nm to 1 $\mu m$. A column of such a hard gel has a high resistance to compression (for example, 1 $kg/cm^2G$ or above), which allows the permeation of a solution to be treated at a high flow rate. Alternately, the porous adsorbent may be in the form of a microfiltration (MF) membrane or an ultrafiltration (UF) membrane.

PHYSICAL FORM AND BASE MATERIAL

The porous adsorbent has a network structure having a number of pores and such a high resistance to compression as not to be broken by liquid flow. Appropriate examples thereof include a hard gel and a microfiltration membrane.

The separating agent comprises a body composed of a porous base material and a functional group of an aliphatic amine group having a chain length of 2 to 50 bonded to the body. The form of the agent depends on the form of the body. The porous base material has a large pore size to accept and adsorb pyrogens of the solution. Particular examples thereof include a gel bead packed in a column and a membrane having a sufficient thickness for fully contacting with the liquid to be treated.

Beads of the gel of the separating agent are preferred to have an average size of 2 to 200 microns. For such gel beads, porous polysaccharide having a size of 50 to 200 microns and an inorganic filler composed of fine particles used in high speed chromatography can be used.

Other suitable examples include an anisotropic ultrafiltration membrane comprising a thin, dense and microporous skin layer portion and a thick and more coarse core portion having larger pores. The above-described membrane structures are known in the art of the separating membrane. The thickness of the membrane is usually 10 to 1000 μm, particularly 50 to 300 μm. If necessary, it is also possible to use a thicker membrane and a plurality of membranes put on top of another.

The porous base material and the adsorbent are specified by the pore size range, and are distinct from other fibers and beads. Non-porous adsorbents such as the above amino-containing fiber and are shown in the comparative example. The pore size of the hydrophilic gel can be determined by the following: a reference solution of a protein or a polysaccharide having a given Stokes' diameter and molecular weight is fed into a column charged with the gel to obtain a standard curve showing a relation between molecular weights and retention volumes and the molecular weights of fractions based on both ends of the curve. For pore sizes Stokes' diameters corresponding to molecular weights are used. For this purpose a commercially available reference kit to determine a filtration molecular weight can be used. If the reference materials happens to react with the functional group of the adsorbent, a determination result for the base material can be used instead. For hydrophobic base materials, a determination result obtained by using a drying method such as the helium method and the mercury method can be used.

The pore size of the adsorbent of the porous membrane is usually in a range found in the so-called ultrafiltration or microfiltration art of membrane separation, e.g., a range from 1 nm to 20 μm, preferably from 10 nm to 5 μm, and a particularly commonly used membrane has a pore size of 50 nm to 1 μm. When a pyrogen is to be removed from a solution containing a drug having a large molecular weight, e.g., protein or polysaccharide, it is a matter of course to select a membrane having a pore size according to the molecular diameter thereof so that the permeation of the drug is not inhibited. The pore size of the membrane is generally expressed in terms of, e.g., a particle diameter having a percentage inhibition of 90% determined from the relationship between the size of the particle not adsorbed on the membrane and the percentage inhibition. The membrane and the beads are similar to each other with respect to the selected pore size. In other words, the pore size of the gel beads ranges from 1 nm to 20 microns, preferably from 10 nm to 5 microns, more preferably from 50 nm to 1 micron. In the case of endotoxin shock, removing pyrogens from blood may be necessary with the use of beads having a large enough pore size for a red blood corpuscle to pass through.

Examples of the porous hard gel base material include beads of hydrophilic synthetic polymers such as cellulose, dextran, polyacrylamide and polyvinyl alcohol and porous silica gel. Agarose and derivatives thereof such as Sepharose are generally soft gels which are unsuitable for high rate liquid-passage treatments since the pores of these substances are broken under the pressure of the liquid flow. When the hard gel of the A-1 type described in the Examples of the present invention is packed in a column (diameter: 1 cm, height: 50 cm) and the pressure loss upon liquid passage is measured, for example, the pressure loss is linear until the flow rate (ml/cm$^2$ hr, the same will apply hereinafter, on the basis of a superficial velocity of a column) exceeds 1500. The pressure loss at a flow rate of 200 is not more than 0.12 kg/cm$^2$, approximately one third of which corresponds to the superficial pressure loss. When a soft gel comprising Sepharose as a base material is similarly packed in a column and a liquid is passed therethrough, on the other hand, a rapid increase in the pressure loss is observed at an extremely lower flow rate. The pressure loss at a flow rate of 200 is 0.8 kg/cm$^2$G. In order to conduct the adsorption/retention efficiently, the pressure loss at a flow rate of, for example, 200 should be 0.5 kg/cm$^2$G or below, preferably 0.25 kg/cm$^2$G or below.

Examples of the porous microfiltration membrane base material include membranes made of various materials such as cellulose membranes, polyvinyl alcohol membranes and polysulfone membranes.

There is no particular limitation on the form of the membrane, and flat membranes, hollow fiber membranes, tubular membranes, etc. may be used. The above-described membranes can be suitably applied in the form of a membrane module. Examples of the membrane module include spiral, preat, plate-and-frame, tubular and hollow fiber modules.

The base material is generally insoluble, i.e., does not dissolve in the liquid to be treated. The solvent is usually water. In special cases, it is also possible to use nonaqueous solvents such as alcohols, acetone, acetonitrile, DMSO and chloroform, or aqueous solutions thereof. It does not matter whether the base material is insoluble or soluble in the course of formation of an adsorbent as far as it becomes insoluble as a final adsorbent having an aliphatic nitrogen-containing functional chain bonded thereto. Many water-insoluble polysaccharide base materials are insoluble also in organic solvents.

The base material is generally a high molecular weight substance and in many cases is a linear organic polymer which is in an aggregated state due to intermolecular forces. The base material has such a structure that an aliphatic nitrogen-containing functional chain can be directly or indirectly immobilized thereto. For example, it has an active site (e.g., active hydrogen) which can react with a functional group such as a hydroxyl or amino group or other substance.

Specific examples of the base material include polysaccharides (including their derivatives such as aminoalkylated polysaccharides and carboxyalkylated polysaccharides, e.g., cellulose and its derivatives, agarose and its derivatives, crosslinked dextran and its derivatives and chitosan as mentioned in the Japanese Patent Laid-Open No. 183712/1982), synthetic organic polymers (e.g., polyacrylonitrile, polysulfone, polyamide, polyvinyl alcohol, polystyrene and polyacrylic resins, hydroxyalkylated, aminoalkylated and halogenoalkylated polystyrene resins, and polyacrylamide resins as mentioned in the same laid-open specification), and inorganic polymers (e.g., silica gel, glass, e.g., aminopropylated porous glass, and various ceramics). Further, it is also possible to select a base material from water-insoluble carriers described in Japanese Patent Laid-Open No. 183712/1982. A functional group useful in the formation of a bond with a ligand, such as hydroxyl or amino group, may be introduced into the above-described base materials by various methods such as methylolation or reduction.

The above-described base material constitutes a particle or a membrane so as to have a three-dimensional structure and is bonded to a nitrogen-containing cyclic compound directly or through a spacer. A molecular structure comprising a base material, a ligand and a spacer has an important effect, together with a higher order structure such as the association of molecules and formation of pores, on the contact of the liquid with the adsorbent. Selection of a proper base material is very important to the practice of the present invention.

BONDING OF FUNCTIONAL CHAIN TO BASE MATERIAL

For example, the bonding method in which a functional chain is directly or indirectly fixed to a carrier comprising a base material constituting a membrane include covalent bonding, ionic bonding, hydrophobic bonding, coordination bonding, etc. Among them, immobilization by means of a covalent bond is desirable because it is less susceptible to elimination of the nitrogen-containing cyclic compound. Examples of the type of covalent bond include amide, ester, ether, amino, imino, sulfide, disulfide and sulfone bonds.

A functional chain or a spacer may be bonded to a base material, e.g., by the following method. A base material is activated with a cyanogen halide (e.g., cyanogen bromide), an epoxy compound (e.g., epichlorohydrin or bisoxirane), a halogenoorganic acid halide (e.g., chloroacetyl chloride or tresyl chloride), a dialdehyde (e.g., glutaraldehyde), benzoquinone or the like, and a nitrogen-containing cyclic compound having an amino group, a hydroxyl group, a thiol group or a carboxyl group, or a spacer is then bonded thereto.

The indirect method for bonding or immobilizing wherein use is made of a spacer carrier, include epoxidation (e.g., epichlorohydrin, bisoxirane), dehydration condensation (WSC, EEDO), reductive amination (NaCN + borane, dimethylamine + borane) and thiol activation (PySSPy). In these methods, a carrier spacer derivative having a group, such as epoxy, carboxyl, amino, hydrazino, formyl or thiol, is converted into an active intermediate by making use of a condensing agent and an activator (as exemplified within the parentheses given after the description of each method) and then is bonded to a ligand having a group such as amino, carboxyl, aldehyde or thiol.

The adsorbent prepared by the epoxidation is superior to the cyanogen bromide method most commonly used in the art in that nonspecific adsorption is low by virtue of more stable immobilization of the ligand, which renders the epoxidation preferable in the present invention.

Examples of the immobilization by other methods than the covalent bonding include immobilization, by means of ionic bonding, an aliphatic nitrogen-containing functional chain having a strongly basic substituent to a carrier having a strongly acidic group bonded to the surface thereof (commercially available as the packing for anion chromatography), and bonding of a base material having a surface which has been made hydrophobic by octadecyl, octyl, phenyl or the like, and a ligand having a long-chain alkyl group or a phenyl group bonded thereto through a hydrophobic bonding (dynamic coating).

Immobilization wherein a base material, a spacer and an aliphatic nitrogen-containing functional chain are bonded to each other is described in detail also in the above-described laid-open specification In the present invention as well, the immobilization of a ligand can be conducted through application of such disclosed technique.

The above-described ligand immobilization technique can be applied to the processing of a material having a membranous shape as described in Example 3 and processing of a material not having a membranous shape as yet shown in Example 1.

FUNCTIONAL CHAIN

The functional chain bonded to the base material of the porous adsorbent has a chain length of 2 to 50, preferably 3 to 35, more preferably 4 to 25, and has a nitrogen-basic group bonded to only an aliphatic carbon atom. The number of the chain-constituting atoms (chain length) of the functional chain means the number of atoms constituting a continuous chain in the longest atom chain. In the case of a functional chain $CH_2CH(OH)CH_2NH(CH_2)_6NH_2$, for example, the number of the chain-constituting atoms is 11, namely, 3 atoms of the intermediate chain (substituted propylene) and 8 atoms of the diaminohexylene.

In the functional group, the nitrogen-containing basic group is attached to only an aliphatic carbon atom. The carbon atom is included, for example, in methylene. It may be a secondary carbon atom or tertiary carbon atom of a branched alkyl group. It preferably is a saturated carbon atom. The nitrogen-containing basic group preferably includes a primary amino, a secondary amino, a tertiary amino, a quaternary ammmonium and imino (=NH). Amidino and guanidino fall in the invention as far as the above shown requirement is met. Isourea does not fall within the scope of the present invention since it is bonded to an oxygen atom. The nitrogen-containing basic group more preferably includes a primary amino and a secondary amino. These are suitably basic and do not offer a steric hindrance. An amide, nitrile and peptide do not fall within the scope of the invention. The first two are too weakly basic and therefore do not adsorb well.

An aliphatic amine group is a preferable embodiment of the functional group of the invention. It is composed of carbon atoms of an alkyl or alkylene group and —NH—. It is stable to an aqueous solution of an alkali. It may contain therein oxygen of an ether and sulfur as well. It may include an ester group and an amide group as far as these groups do not have a bad influence on the invention. It is made distinct from prior functional groups such as heterocyclic chain groups, aromatic amine groups and peptide groups.

In the functional group of the invention, the nitrogen atom attached only to an aliphatic carbon atom is defined a an aliphatic nitrogen atom.

The nitrogen atom may be either a terminal constituting atom or an intermediate one. Alternately, it may be a pendant-type nitrogen atom which is bonded to an intermediate atom either directly or via another aliphatic carbon atom.

The functional chain preferably involves a primary or secondary amino aliphatic nitrogen atom and a chain having 3 or more carbon atoms adjacent thereto. In the case of the above-cited functional chain, a hexylene group (and a hydroxyl-substituted propylene group) are adjacent to two nitrogen atoms.

The functional group is substantially a chain-like compound having a relatively short chain length. It is different from a group having a cyclic structure in its main body from the viewpoint of the functional nitrogen atom, such as a nitrogen-containing heterocyclic compound and an aromatic amine. A group having a cyclic structure at a position not adjacent to the functional nitrogen is included in the invention, such as a benzylamine.

A typical example of the functional chain comprises an intermediate chain directly bonded to a base material and a nitrogen atom-containing moiety. Typical examples of the moiety containing an aliphatic nitrogen atom include those derived from alkylenediamine or open-chain basic amino acids, though a single amino acid may be used therefor. The molar ratio of the intermediate chain to the aliphatic nitrogen atom-containing moiety is not necessarily 1:1.

The chemical structures of adsorbents having an intermediate chain may be schematically classified as follows:

| Base material | Intermediate chain |
|---|---|
| | Nitrogen-containing moiety; |
| Base material | Intermediate chain |
| | Nitrogen-containing moiety |
| | Intermediate chain - Base material; |
| Base material | Intermediate chain |
| | Nitrogen-containing moiety A |
| | Nitrogen-containing moiety B; and |
| Base material | Intermediate chain |
| | Nitrogen-containing moiety. |

When hexamethylenediamine is reacted with an epoxymethylated base material, for example, the adsorbent of the first type (1:1 reaction product) has a primary amino group and a secondary amino group at a molar ratio of 1:2 whereas that of the second type (1:2 reaction product) exclusively has secondary amino groups. It is sometimes observed in practice that both of these reactions simultaneously proceed and thus these reaction products are obtained in the form of a mixture. The composition of this reaction product mixture may be determined by analyzing the amino groups. In some cases, these adsorbents are not largely different from each other in performance. However it is sometimes observed that a mixture containing a larger amount of the second type product is superior in performance to another one.

The length of the intermediate chain, which usually ranges from 2 to 10, may be prolonged by inserting, for example, a spacer, if required. When epichlorohydrin is used, an intermediate of a chain length of 3 is formed as the major product. However there are observed adducts carrying a plurality of epichlorohydrin molecules which are formed as side products or with the intention.

Now a method for bonding a functional chain to a base material will be illustrated, by way of example, with the use of a polyhydroxyl polymer as the base material. The base material may be selected from among those inherently having a large number of hydroxyl groups (for example, polysaccharides, polyvinyl alcohol polymers, or silica gel) and those obtained by introducing a large number of hydroxyl groups into other polymers. The aliphatic nitrogen atom-containing moiety may be directly bonded to the base material. For example, an aminoalkylcellulose may be obtained by reacting cellulose with an aminoalkyl chloride. In many cases, however, the nitrogen atom-containing moiety is bonded to the base material by using a binding agent. As the binding agent, epichlorohydrin, glutaraldehyde, or cyanogen bromide may be used to give an intermediate having a chain of 3, 5 or 1 carbon atom, respectively, as mentioned above.

In order to form the nitrogen atom-containing moiety, compounds having a plurality of amino groups, such as basic chain amino acids, or compounds having a single amino group, such as aminoalkyl chlorides, may be employed. In the simplest case, the object may be achieved by using ammonia.

As the result of these reactions, the functional chain having an amino group and the carbon chains adjacent thereto are bonded to the base material. The carbon chains may be located either between the nitrogen atom and the base material or on the opposite side. As described above, the functional chain may be arranged in such a manner as to crosslink the base material.

Now examples of the functional chain will be given.

The following aliphatic chains A to D are particularly shown below.

A: $—CH_2CH(OH)CH_2NHR$

Examples of R are hydrogen atom and the following (In brackets is the name of the compound $RNH_2$ or ROH which correspond to R).

$C(—NH)NH_2$[guanidine]; $(CH2)_n$ $NH_2$ (n=1-12, e.g., 6)

[alkylenediamine], $COCH(NH2)(CH2)_4$ $NH_2$ [lysine], $COCH(NH2)(CH2)_3$ $NH_2$ [ornithine], $COCH(NH2)(CH2)_3$ $NHC(—NH)NH_2$[arginine].

There are used natural polyamines such as spermidine and spermine, which are straight polyamines having both terminal $NH_2$ groups and intermediate $CH_2$ and NH groups and have a chain length of up to 17.

B: $—CH_2—CH(OH)CH_2—NH(CH_2)_5NHR$

Examples of R: $(CH2)_n$ $NH_2$ (n=1-12), $(CH_2)_n—NH-C(—NH)NH_2$ (n=1-12)

C: $—CH_2—CH(OH)CH_2—NHCOCH_2CH_2CONHR$

Examples of R: $(CH2)_n$ $NH_2$ (n=1-12), $(CH_2)_n$ $NHC(—NH)NH_2$ (n=1-12)

D: $—CH_2—CH(OH)CH_2—NH—(CH_2)_6NHR$

Examples of R: $C(—NH)NH_2$, $COCH(NH_2)(CH2)_4$ $NH_2$, $(CH_2)_nNH_2$ (n=1-12)

The following amine chain in which R is hydrogen, an alkyl or an alkyl substituted by an aliphatic nitrogen basic functional group and A is hydrogen or methyl may be used.

$—CH_2)_nNHR$

When R is hydrogen and n is two, the chain length is shortest, that is , 2. This chain having a chain length of 3 or more is more stable. For example porous aminohexylcelluloselose is made of the chain having n of 6, bonded to a porous cellulose.

$—(CH_2CH_2NH)_nR$ $—(CH_2—CAH—O)_n—CH_2—CHA—NHR$ $—CH_2CH(OH)CH_2—O—(CH_2)_n—C_6H_4—(CH_2)_m—NHR$ $—C(=NH)—NH—(CH_2)_nNHR$

TYPICAL SEPARATING AGENT

A typical separating agent comprises cellulose as a base material and an aliphatic chain of the above-mentioned $—CH_2CH(OH)CH_2NHR—$ type. A separating agent wherein R is H may be obtained by condensing epichlorohydrin with the base material and opening the ring with ammonia. A separating agent shown as the B-1 type in the Examples is of this type having cellulose as the base material. It is in the form of a gel bead having a particle size of from 50 to 200 μm and a pore size of from approximately 100 to 500 nm.

Separating agents of the given types (other than those wherein R is H) may be obtained by reacting these separating agents of the B-1 type or intermediate products obtained during the preparation thereof with various compounds given in the brackets in the above description. A separating agent shown as the A-1 type is a cellulose derivative having an aliphatic chain $CH_2CH(OH)CH_2NH(CH_2)_6NH_2$ which is obtained by the ring-opening reaction of a cellulose/epichlorohydrin condensate with hexamethylenediamine. The separating agent of the A-1 type may be reacted with lysine, 0-methylisourea or arginine to thereby give the A-2, A-3 or A-4 type, respectively. Further, the separating agent of the B-1 type may be reacted with lysine, 0-methylisourea or arginine to thereby give the B-2, B3 or B-4 type, respectively.

Furthermore, separating agents wherein agarose is used as the base material instead of cellulose may be used. However, these separating agents are in the form of a soft gel which is unsuitable for the application at a high flow rate.

Examples of the separating agent comprising a synthetic resin as the base material are as follows.

Polystyrene:

The benzene ring of a styrene/DVB copolymer is chloromethylated at the p-position and reacted with triethylamine. The reaction product is further reacted with hexamethylenediamine to thereby give a separating agent wherein a functional chain $CH_2NH(CH_2)_6NH_2$ is bonded to a base material of a polystyrene resin.

Hydrophilic vinyl polymer:

In the production process of the above-mentioned separating agent of A-1 type, Epoxy Toyo Pearl 650M (a product of Toyo Soda Mfg. Co., Ltd.) is used as a base gel instead of the cellulose/epichlorohydrin condensate. When the obtained product (particle size: 44 to 88 μm) is packed into a column (inner diameter: 16 mm, height: 150 mm), a liquid can be treated under a pressure of 0.2 kg/cm$^2$G at a flow rate of 0.5 1/hr (SV=17).

PVA:

A PVA separating agent in the form of a membrane is shown in Example 3. The separating agent may be in the form of a bead.

Polysulfone:

A functional chain may be easily bonded to, for example, a polysulfone MF membrane having an amino group commercially available as a carrier for immobilizing an enzyme. After activating with glutaraldehyde, the membrane is reacted with a compound having a aliphatic nitrogen atom. By using hexamethylenediamine, a functional chain having 5- and 6-carbon chains adjacent to the nitrogen atom may be formed.

TREATMENT METHOD

Now liquids to which the present invention is to be applied will be classified into 4 types and the treatment methods and separation performances thereof will be described.

Case 1: Sample Containing an Acidic Polymer

A typical example of this type is a solution of an acidic protein (for example, HSA). Although both a pyrogen and a drug are negatively charged, the binding force of the pyrogen to a separating agent is stronger, which enables selective adsorption. In order to achieve the selective adsorption, it is preferable to control the ionic strength to be on a somewhat higher level ($\mu=0.02$–$0.2$). When the efficiency of the removal of the pyrogen is poor, the ionic strength is adjusted to 0 02 to 0.07 and the treatment is effected around the isoelectric point of the drug, if required. When the percentage recovery of the drug is low, the amount of the employed adsorbent is minimized within the acceptable range and the treatment is effected below the isoelectric point of the drug.

Case 2: Sample Containing a Basic Polymer

This is the most difficult case, since a drug or a contaminant is positively charged and thus has an affinity for a pyrogen. It is preferable to effect the adsorption of the pyrogen at an ionic strength of 0.1 or below. When the affinity of the basic material to the pyrogen is high, however, it is sometimes required to elevate the ionic strength. When the efficiency of the removal is poor, the treatment is effected within a range from pH 8 to the isoelectric point of the sample. However care should be taken in this case, since the solubility of the sample is lowered around the isoelectric point.

Case 3: Gammaglobulin Preparation, etc.

It is preferable to treat a neutral high-molecular weight protein at around pH 7 and at an ionic strength of 0.1 or above. When the pH is lowered to approximately 5, a pyrogen is adsorbed by globulin. Thus the removal extent sometimes lowers.

Case 4: Dialyzate, Saccharide, Amino Acid Transfusion, etc.

The pH may preferably range from 3 to 10. The efficiency of the removal of a pyrogen is not affected by the ionic strength. When contaminated with a basic and low-molecular weight organic material, however, it is preferable to adjust the ionic strength to 0.02 or above.

SEPARATING FUNCTION

The porous adsorbent of the invention can selectively adsorb and separate a phosphopolyol such as pyrogen(s) from a solution of a physiologically active substance. The physiologically substance includes for example an amino acid such as histidine, alanine and proline, a nucleic acid base such as adenine and cytosine, an antibiotic such as penicillin G, a hormone such as insulin, a vitamin such as flavin, adenine and dinucleotide, a seroprotein such as albumin and gamma-globulin, an enzyme such as urokinase, asparaginase and lysozyme, an antibody such as immunoglobulin and vaccine such as flu vaccine. The invention applies to an injection liquid such as dextrane, fructose and glucose, a sodium citrate solution for blood transfusion, an intravenous drip and a supplemental liquid for artificial kidneys of the filtration type. The applicable liquid may have different values of ion strength an concentration. The liquid to administer directly to a living body usually has an ion strength of about 0.15 like physiological saline.

The concentration of a pyrogen contaminating the liquid to be treated widely varies from case to case. Said concentration may preferably several tens of μg/ml or below. In particular, the separating agent of the present invention can adsorb and remove a pyrogen in a trace amount (i.e., 100 ng/ml or below). When the pyrogen concentration in a drug is extremely high, it is sometimes effective to perform a pretreatment with the use of, for example, an UF membrane before using the separating agent of the present invention.

When the base material is in the form of a gel, the treatment with the use of the separating agent of the present invention may be effected either by a batch-type method or a column-type one.

The method for separation of pyrogen according to the invention may depend on the concentration of the pyrogen. A liquid having a relatively low content of pyrogen, for example 500 EU per ml, can be effectively treated with a membrane having a normal thickness. A pyrogen liquid having a high content can be treated with a thick membrane or laminates of membranes, in a manner such that the pore size causes an effective separation at the feeding side having the higher concentration and then adsorption causes separation at the discharging side having the lower concentration. This shows one treatment working both ways. No pre-treatment is needed.

In the present invention, a pyrogen is usually separated from a solution of a high ionic strength through adsorption and retention. Such an adsorption/retention method may be distinguished from a chromatographic separation method where adsorption and elution are parallelly effected. In the case of a drug having a particularly high affinity for an adsorbent, a poor percentage recovery is sometimes observed. In this case, the adsorbent which has adsorbed a pyrogen together with the drug is treated with a solution of a higher ionic strength. Thus the drug may be selectively eluted and recovered.

RESISTANCE TO ALKALI AND REPRODUCTION

The separating agent of the invention can be reclaimed and reproduced from the used one having adsorbed pyrogens under the alkaline condition. Moreover it is very stable against an alkali. It remains as it is in view of the separating property even after it has been allowed to stand in 2N NaOH, its 20% ethanol-containing aqueous solution, for one month. It can be reclaimed at least ten times without change in its separating performance and resistance to alkali, in comparison with a prior agent having a functional group of a peptide. This can be experimentally confirmed by using the determination method shown in Example 16.

The present invention provides a separation method whereby a phosphopolyol compound can be effectively removed from a solution of a high ionic strength with the use of a separating agent having a specific structure. This method is excellent in percentage removal, ultimate concentration, percentage drug recovery, etc., and highly safe. Some of the separating agents to be used in this method have been known per se as a substance or suggested as an intermediate in a synthesis pathway. Some of the separating agents are furthermore known as a separating agent available for different purposes, for example, as a carrier in analytical chromatography. However, some typical separating agents have not been known hitherto as a separating agent. Accordingly, the present invention further provides a novel separating agent.

The use of the separating agent of the present invention makes it possible to remove a pyrogen from a solution of a relatively high ionic strength and, furthermore, to remove a pyrogen from a solution containing a drug such as a protein at an efficiency of as high as 99% by a single batchwise treatment. That is to say, the treatment with said separating agent can reduce the pyrogen concentrations in a solution of 100 ng/ml and 1 ng/ml, respectively, to 1 ng/ml and 10 pg/ml. In the case of a solution free from any drug such as a protein, a pyrogen concentration of 100 ng/ml can be reduced to 1 pg/ml or below (below detection limit) by a single batchwise treatment, which corresponds to a percentage removal of 99.999% or above.

In addition, the separating agent of the present invention is effective over a wide pH range as compared with conventional pyrogen adsorbents. The applicable pH range thereof may vary depending on the ionic strength. For example, it may be used within a pH range of from 3 to 11 at an ionic strength of 0.1.

The mechanism of the function of the separating agent of the present invention has not been clarified in detail as yet. However the present inventors assume the mechanism functions as follows.

Namely, the separating agent, which comprises a base material and a functional aliphatic chain, comes in close contact with a liquid passing through its pores and thus selectively adsorbs and retains a pyrogen. The base material consists of macromolecules and thus the separating agent remains insoluble as a whole. However, the base material is porous and, further, the aliphatic chain has some degree of freedom in steric structure. Namely, the separating agent has a structure suitable for accepting large molecules (such as pyrogens or nucleic acids) and exerting the adsorption effect by appropriately controlling the location of the functional chain. Some conventional adsorbents, for example, basic ion exchange resins comprise a macroporous base material to which an amino group is bonded. Although such an adsorbent is capable of removing a pyrogen contained in water, it cannot selectively adsorb a pyrogen contained in a drug-containing solution at a high removal efficiency of 99%, since it lacks any degree of freedom in the structure.

The functional aliphatic chain in the present invention is an aliphatic chain consisting of 3 to 50 atoms. When applied to a solution of a high ionic strength, it exerts a particularly excellent effect as compared with a conventional pyrogen separating agent comprising a nitrogen-containing cyclic compound as a functional chain. Since the functional chain of the present invention carries 3 or more constituting atoms, the functional chain has a degree of freedom which cannot be expected in the case of an ion exchange resin wherein an amino group is directly bonded to the polystyrene aromatic nucleus of a base material (chain-constituting atom number: 0). On the other hand the number of chain-constituting atoms in the present invention is much smaller than that of polymyxin (an antibiotic) and a relatively simple molecule may be employed as an aliphatic chain. Therefore, even when the aliphatic chain should happen to be liberated from the base material and enter into the liquid to be treated, little serious physiological side effect should occur.

In the present invention, a nitrogen-containing aliphatic chain having a short chain length and a relatively simple structure is to be bonded to the base material. Therefore, a separating agent of the desired adsorption performance may be obtained by varying the structure of the nitrogen-containing aliphatic chain structure depending on various combinations of pyrogens and drugs. A crosslinked graft copolymer having a large molecular weight observed in some prior arts is a mixture of complicated structures and thus involves many factors affecting the performance thereof. In this case, therefore, it seems to be difficult to develop various series of products satisfying various needs, unlike the case of the present invention.

The separating agent of the present invention having the above-mentioned construction can be used in, for example, the batch-treatment of a human serum albumin solution of an ionic strength of 0.16 [a sample prepared by adding 100 ng/ml of *E. coli* 0111:B4 (extracted with phenol) and common salt to commercially available HSA (concentration: 5%)] to thereby remove 90 to 99% of the pyrogen.

EXAMPLES

In the following description, the expression "(wet)" refers to "wet weight" as a rule, though analytical data are given on a dry weight basis.

EXAMPLE 1

Separating Agent A-1 type:

After washing with water and dehydrating by filtering by suction (2 minutes), 50 g (wet) of a porous cellulose gel carrier (a) in the form of a bead was dispersed in 110 ml of 0.6N caustic soda. 16 ml of epichlorohydrin was added thereto and the mixture was allowed to react at 60° C. for 30 minutes followed by filtering and washing with water. To the epoxy-activated intermediate (b) thus obtained was added a ligand solution prepared by dissolving 4 ml of 65 hexamethylenediamine in 100 ml of water. The resulting mixture was then allowed to react at 70° C. for 1 hour, filtered and washed with water. After adjusting the pH value to 10.4 with hydrochloric acid, the reaction mixture was washed with water and dehydrated. Thus approximately 55 g of a wet adsorbent of A-1 type (c) was obtained.

g/wet/g dry (a) 17.0, 1.82 ml/g wet (b) 15.8, epoxy content (μmol/g dry) 174

(c) 18.2, 1.45 ml/g wet, hexamethylenediamine content (μmol/g dry) 133 (elemental analysis).

This separating agent had a $CH_2CH(OH)CH_2NH(CH_2)_6NH_2$ chain (chain length: 11) as the major functional chain.

Similarly, a separating agent having a hexamethylenediamine content of 50 to 600 may be obtained by varying the reaction conditions. Some of the separating agents thus obtained by varying the reaction conditions may carry both of a $CH_2CH(OH)CH_2NH(CH_2)_6NHCH_2CG(OH)CH_2$ chain (chain length: 14) and a $CH_2CH(OH)CH_2NH(CH_2)_6NH_2$ chain (chain length: 11) as the major chain.

A-2 type:

Obtained by condensing a separating agent of the above A-1 type with lysine.

Functional chain: $CH_2CH(OH)CH_2NH(CH_2)_6NH$-$COCH(NH_2)(CH_2)_4NH_2$.

A-3 type:

Obtained by condensing a separating agent of the above A-1 type with O-methylisourea to thereby give a guanidine terminal.

Functional chain: $CH_2CH(OH)CH_2NH(CH_2)_6NHC(=NH)NH_2$.

B-1 type:

Obtained by adding epichlorohydrin and ammonia to a porous cellulose gel as a base material.

Functional chain: $CH_2CH(OH)CH_2NH_2$, $CH_2CH(OH)CH_2NHCH_2CH(OH)CH_2$.

In the form of a bead of a particle size of approximately from 50 to 200 μm and a pore size of approximately from 100 to 500 nm.

B-2 type:

Obtained by condensing a separating agent of the above B-1 type with lysine.

Function chain: $CH_2CH(OH)CH_2NH$-$COCH(NH_2)(CH_2)_4NH_2$.

B-3 type:

Obtained by condensing a separating agent of the above B-1 type with O-methylisourea.

Functional chain: $CH_2CH(OH)CH_2NHC(=NH)NH_2$.

Commercially available adsorbent:

Each having a high percentage removal of a pyrogen.

IRA:

Weakly basic cation exchange resin Amberlite (trademark) IRA-98. Comprising macroporous polystyrene beads as a base material and a dimethylamino group directly bonded to the aromatic nucleus as a ligand.

TEAE and DEAE:

Cellulosic ion exchange materials manufactured by Serva Co. comprising microfibrous cellulose (not porous but microgranulate). The ligand of TEAE is $OCH_2CH_2N^+(C_2H_5)_3$ obtained by substituting the OH group of cellulose while that of DEAE is $OCH_2CH_2N(C_2H_5)_2$ which respectively show strongly basic and moderately neutral properties.

BCW:

Chitosan beads BCW series 2503 (products of Fuji Spinning Co., Ltd.). Strongly basic anion exchange resin obtained by chemically binding a quaternary amine to a chitosan bead.

LIQUID TO BE TREATED

Test solution 1: commercially available HSA (human serum albumin, concentration: 5%, ionic strength $\mu=0.02$) containing 100 ng/ml of standard endotoxin *E. coli* 0111:$B_4$.

Test solution 2: commercially available HSA (concentration: 20%, ionic strength $\mu=0.07$) containing 100 ng/ml of standard endotoxin *E. coli* 0111:$B_4$.

Test solution 3: prepared by adding common salt to the test solution 1 to thereby adjust the ionic strength to 0.16.

Test solution 4: prepared by adding common salt to commercially available HSA (concentration: 5%) to thereby adjust the ionic strength to 0.16 and then adding 1 ng/ml of *E. coli* 0111:$B_4$.

Test solution 5: prepared by adding 100 ng/ml of *E. coli* 0111:$B_4$ to pyrogen-free water.

REMOVAL OF PYROGEN (BATCH METHOD)

Test method: 1 ml of each test solution and 100 mg (wet) of a separating agent were stirred in a pyrogen-free glass test tube at room temperature at 50 rpm for 1 hour. Next, the concentration of the pyrogen remaining in the solution was determined by turbidmetry by making use of Limulius ES-test, Wako (trademark) and Toxinometer-ET-201(each a product of Wako Pure Chemical Industries, Ltd.) and thus the percentage pyrogen removal was calculated therefrom. The percentage HSA recovery was determined by PC analysis.

Results: Table 1 summarizes the results of the treatment of the test solutions with the use of various separating agents. The separation method of the present invention shows an excellent pyrogen removal performance in a higher ionic strength region.

TABLE 1

| | | A-1 | B-1 | A-2 | B-2 |
|---|---|---|---|---|---|
| Test solution 1 | Percentage removal | 36 | 34 | 81 | 69 |
| | Percentage recovery | 72 | 98 | 68 | 90 |
| Test solution 2 | Percentage removal | 95 | 90 | 91 | 81 |
| | Percentage recovery | 95 | 101 | 102 | 102 |
| Test solution 3 | Percentage removal | 93 | 99 | 98 | 86 |
| | Percentage recovery | 84 | 100 | 96 | 96 |
| Test solution 4 | Percentage removal | 97 | 99 | | |
| | Percentage recovery | 92 | 100 | | |
| Test solution 5 | Percentage removal | >99.999% in each case | | | |

COMPARATIVE EXAMPLE 1

The test solution 2 was treated in the same manner as the one described in Example 1 by using commercially available ion exchange materials. As a result, some of the ion exchange materials showed an effect of removing pyrogens to a certain extent. However none of them achieved a percentage removal of 90% or above.

TABLE 2

| | | IRA | TEAE | DEAE | BCW |
|---|---|---|---|---|---|
| Test solution 1 | Percentage removal | 5 | 0 | 0 | |
| | Percentage recovery | 98 | 97 | 99 | |
| Test solution 2 | Percentage removal | 76 | 30 | 0 | 47 |
| | Percentage recovery | 97 | 97 | 99 | 94 |

EXAMPLE 2

By using 0.1 g (wet) of a separating agent of A-1 type, the performance of removing natural pyrogens contained in 2 ml of an aqueous drug solution was examined by a batch adsorption method.

Table 3 shows the employed samples, treatment conditions and the obtained results.

TABLE 3

| Item (unit) Sample | Concn. (%) | pH | Ionic strength (μ) | Pyrogen concn. after treat. | Pyrogen concn. before treat. | Removal (%) | Sample recovery (%) |
|---|---|---|---|---|---|---|---|
| Bovine serum albumin | 10 | 0.8 | 0.18 | 7.85 | 0.82 | 90 | 100 |
| Lysozyme | 0.5 | 9.0 | 0.05 | 9.66 | 0.09 | 99 | 94 |
| Cytochrome C | 0.5 | 9.0 | 0.05 | 4.11 | 0.09 | 98 | 98 |
| Human Y-Globulin | 1.0 | 8.5 | 0.22 | 0.87 | 0.08 | 92 | 100 |

EXAMPLE 3

Preparation of PVA Membrane Containing Nitrogen-Containing Aliphatic Chain

Three polyvinyl alcohol (PVA) hollow fiber membranes (Kuraray SF-401; a homogeneous membrane having a pore size of about 0.1 μm; 330 μm in inner diameter, 125 μm in membrane thickness and 5.5 cm in effective length) were fixed to a glass tube with an epoxy resin to prepare a miniature module. Then, the hollow fiber membranes are brought into contact with liquids in the order of steps (1) to (5) by making use of the module as prepared above to subject the membrane to various treatments including a chemical reaction of a material constituting the membrane, thereby preparing the AH-PVA membrane adsorbent of the present invention. In this case, the membrane is brought into contact with the liquid by circulating the liquid in and outside the hollow fiber membrane at a flow rate of 20 to 50 ml/min. The temperature is adjusted by immersing the whole module in a water bath.

(1) washing (1M NaCl, pure water), (2) epoxidation (60° C. in 90 ml of 1 N NaOH; further 10 ml of epichlorohydrin is added and the system is kept at that temperature for 2 hr), (3) washing (pure water), (4) spacer bonding (40 ml of 0.625% aqueous hexamethylenediamine solution, 60° C., 2 hr), (5) washing (pure water). The AH-RVA membrane for the adsorbent was prepared.

Elementary analysis values (%) of AH-PVA are shown below, with those of PVA membrane.

| Sample | Carbon | Hydrogen | Nitrogen |
|---|---|---|---|
| PVA membrane as raw material | 55.14 | 7.92 | 0.02 |
| AH-PVA membrane | 54.92 | 8.00 | 0.17 |

EXAMPLE 4

Removal of Pyrogens 50 ml of an untreated water including a pyrogen coming from *E. coli* 0111:B4, 1 ng or 5.5 EU, at a concentration of 3300 EU/ml is circulated through the AH-PVA membrane obtained in Example 3, having 1.7 $cm^2$ in area and incorporated into the miniature module, at a flow rate of 13 ml/min, and the membrane permeation rate is adjusted to 0.2 ml/min (70 $l/m^2 \cdot hr$) by means of a pressure cock. The supply pressure is about 0.2 $kg/cm^2G$. The pyrogen concentration of the permeated liquid is measured by making use of Limulus ES-test, Wako (trademark) and Toxinometer-ET-201 (each a product of Wako Pure Chemical Industries Ltd.).

When the amount of the permeated liquid is 25 ml, the pyrogen concentration and percentage removal of pyrogen are 0.33 EU/ml and 99.99%, respectively.

For comparison, the same test is conducted by making use of the same PVA hollow fiber membrane miniature module as that used in Example 3 as a starting material in the preparation of the adsorbent. The pyrogen concentration of permeated water and percentage removal of pyrogens obtained by normal membranes separation are 627 EU/ml and 81%, respectively.

EXAMPLE 5

Treatment of Physiological Saline

A 0.9% saline including 4630 EU/ml of pyrogens ($\mu$=0.15) is treated with the membrane AH-PVA of Example 4, 1.7 cm$^2$ in area, resulting in 0.08 EU/ml of pyrogens and a removal extent of 99.998%. A comparison by the PVA membrane results in 1120 EU/ml of pyrogens and a removal extent of 76%.

EXAMPLE 6

Treatment of Cytochrome C having a Molecular Weight of about 12,500

200 ml of 10.0% Cytochrome C including 1130 EU/ml of pyrogens, at a pH of 9.0 and $\mu$ of 0.02, is treated in the same way as shown in Example 4, using the AH-PVA membrane of Example 3, having an effective surface area of 50 cm$^2$. The circulation rate is 100 ml/min and flux is 4.5 ml/min. Results are that the treated liquid has a pyrogen content of 0.23 EU/ml, removal extent is 99.98% and d Cytochrome content of 10.0%. The rabbit test result is negative. A comparison by the PVA membrane results in a removal extent of 45% and a pyrogen content of 622 EU.

EXAMPLE 7

Treatment of Human Seroalbumin (HSA)

100 m of 20% HSA at a pH of 6.5, at a $\mu$ of 0.07 and including 85 EU/ml of pyrogens, was treated with the AH-PVA membrane module of Example 6, resulting in a pyrogen content of 0.84 EU/ml and a removal extent of 99%. A comparison by the PVA membrane results in 75 EU/ml of pyrogens and a removal content of 12%.

EXAMPLE 8

Effect of Ionic Strength; pH Value: 7 in Each Case

To 1-ml portions of saline solutions containing 100 ng/ml of a pyrogen at various concentrations were added 0.1-g portions of a separating agent of A-1 type. After stirring at 25° C. for 1 hour at 25 rpm, the adsorption ratio for each separating agent was determined from the pyrogen concentration of the supernatant. The relationship between the ionic strength and pyrogen adsorption ratio was as follows. Thus, it was confirmed that the separating agent gave high adsorption ratios over a wide range of ionic strength.

| | 0.1 | 0.2 | 0.35 | 0.7 | 1.2 | 1.7 | 2.0 |
|---|---|---|---|---|---|---|---|
| Adsorption ratio (%) | 99.98 | 99.3 | 98.2 | 97.8 | 97.5 | 96.5 | 97.9 |

The pyrogen employed above was one originating from *E. coli* 0111:B4.

COMPARISON

When a separating agent comprising a nitrogen-containing cyclic compound as a ligand was employed, the adsorption ratio showed a decrease at a lower ionic strength. The limit thereof varied depending on the employed pyrogen. In the case of a pyrogen originating from *E. coli* UKT-B, for example, an adsorption ratio of 100% was maintained until the ionic strength reached 0.1 and then reduced to 82% when $\mu$ was 0.2 and to 5% when $\mu$ was 0.3. In the case of a pyrogen originating from *E. coli* 0128:B12, on the other hand, the adsorption ratio was 40% when $\mu$ was 0.1 while it was 0% when $\mu$ was 0.2.

EXAMPLE 9

Effect of pH

Aqueous pyrogen solutions (1000 ng/ml) varying from each other in pH value ($\mu$=0.1) were tested in the same manner as the one described in Example 8. The employed pyrogen, the concentration thereof and the employed separating agent were the same as those described in Example 8. The relationship between the pyrogen adsorption ratio and pH value was as follows. Thus an adsorption performance over a wide range of pH value was confirmed.

| pH | 2.9 | 5.4 | 6.8 | 8.1 | 9.2 | 10.7 | 11.7 |
|---|---|---|---|---|---|---|---|
| Adsorption ratio (%) | 99.8 | 99.96 | 99.9 | 99.96 | 99.7 | 99.3 | 98.8 |

COMPARISON

When a separating agent comprising a nitrogen-containing cyclic compound as a ligand was employed, the adsorption ratio showed a decrease at a lower pH value. At an ionic strength of 0.1, the adsorption ratio remained 100% at a pH value of 7 or below and decreased to approximately 90% at pH 8 and 0% at pH 9. When $\mu$ was 0.02, the adsorption ratio remained 100% at pH 8 or below and decreased to approximately 65% at pH 9. (The employed pyrogen was one originating from *E. coli* UKT-B).

EXAMPLE 10

Dialyzate

The pyrogen concentration of a dialyzate was adjusted to 1440 pg/ml by adding a standard pyrogen. The obtained dialyzate was collected in a sterile polystyrene test tube and an adsorbent, 0.1 time as much as the dialyzate, was added thereto. After stirring in a round mixer for 20 minutes, the mixture was filtered and the pyrogen concentration was measured.

After being treated with a separating agent of A-1 type, the pyrogen concentration was reduced to 1.5 pg/ml. After being treated with a separating agent of B-1 type, it was reduced to 185 pg/ml. Thus, it seems that the separating agent of A-1 type is superior to the one of B-1 type in the adsorption rate.

EXAMPLE 11

Column Method

Two adsorbents showing excellent results in the test performed in Example 10 were employed in the determination of a pyrogen concentration of an eluate by the column method.

Column: inner diameter: 10 mm, packing height: 80 mm (8.3 ml).

Test solution: prepared by adjusting the pyrogen concentration of a dialyzate to 1 ng/ml by adding *E. coli* 0111:B4.

| Flow rate (cm/hr) | 76 | 153 | 306 | 535 | 764 | 994 | 1300 |
|---|---|---|---|---|---|---|---|
| A-1 adsorbent | 2 | 3 | 6 | 11 | 18 | 37 | 57 |
| nonpolar adsorbent (XAD-2) | 90 | 105 | 159 | 256 | 348 | 388 | 482 |

Although XAD-2 showed an excellent result (4 pg/ml next to the A-1 adsorbent, it was largely inferior to the A-1 adsorbent in adsorption performance at a high SV.

EXAMPLE 12

Comparative Example

Cellulose beads were first reacted with epichlorohydrin and then with polyallylamine hydrochloride (molecular weight: 60,000) to thereby give a porous adsorbent AA-C. Separately, polyethyleneimine (molecular weight: 40,000–50,000) was treated in the same manner to thereby give a porous adsorbent PEI-C. Furthermore, commercially available polyallylamine beads were referred to as PAA-B. The beads of these three types were subjected to an adsorption test to a batch method shown in Example 8.

Each of these samples well adsorbed pyrogens in physiological saline but the pyrogen adsorption ratio in a 5% HSA solution was lower than 50%. the relationship among the ionic strength of test solution, pyrogen concentration (ng/ml) of test solution and pyrogen concentration (ng/ml) of treated solution was as follows.

| | $\mu$ | Test solution | AA-C | PEI-C | PAA-B |
|---|---|---|---|---|---|
| Phys. saline | 0.15 | 192 | 0.015 | 0.012 | 0.11 |
| 5% HSA | 0.02 | 2.50 | 4.12 | 2.34 | 2.40 |
| 5% HSA | 0.09 | 4.06 | 2.02 | 2.50 | 3.14 |

EXAMPLE 13

Column Method

By using an adsorbent of A-1 type, a pyrogen in an HSA solution was removed by the column method.

Test solution: 5% HSA + 2M NaCl + *E. coli* 0111:B4 (DIFCO), PH 6.4, $\mu$=0.15.

Treatment method: after equilibrating the column, the flow rate (SV) was varied from 30 to 2 and the pyrogen concentration of the treated solution was determined.

Column: inner diameter: 10 mm, height: 60 mm.

| | Results: | |
|---|---|---|
| | Pyrogen concn. (pg/ml) | Percentage removal (%) |
| Test solution | 7300 | |
| 30 | 801 | 95.9 |
| 10 | 96 | 98.7 |
| 5 | 74 | 99.0 |
| 2 | 69 | 99.1 |

EXAMPLE 14

To 2 ml of a test solution prepared by adding *E. coli* 0111:B4 (DIFCO) to a 0.9% NaCl solution was added 0.2 g (wet) of an adsorbent. After stirring for 1 hour, the mixture was filtered and subjected to Limulus ES-test.

| | | |
|---|---|---|
| Pyrogen concn. in test solution (pg/ml): | 17000 | 13000 |
| After treating with A-1 adsorbent: | 5 | not detected |

EXAMPLE 15

To a phosphate buffer solution (pH=7, $\mu$=0.02) containing pyrogens originating from various microorganisms was added 0.2 g (wet) of an A-1 adsorbent. After treatment at 25° C. at 25 rpm for 1 hour, the mixture was filtered through a filter (22 $\mu$m) and the pyrogen concentrations were determined.

Determination method: Endospacy method (MP).

Further, a sample obtained by adjusting the ionic strength to 0.1 with common salt was tested.

| Pyrogen | Ionic strength | E.U./ml Applied | E.U./ml Unbound |
|---|---|---|---|
| *E. coli* 0111:B4 | 0.02 | 5510 | 0.06 |
| | 0.1 | 4630 | 0.08 |
| *E. coli* UKT-B | 0.02 | 3900 | 0.28 |
| | 0.1 | 4070 | 0.62 |
| *S. enteritidis* | 0.02 | 6280 | 0.12 |
| | 0.1 | 9440 | 0.59 |
| *S. flexneri* | 0.02 | 9440 | 0.07 |
| | 0.1 | 4880 | 0.07 |
| *P. aeruginose* | 0.02 | 1230 | 0.04 |
| | 0.1 | 380 | 0.05 |

EXAMPLE 16

0.5 g (wet) of an A-1 adsorbent was contacted with a liquid containing pyrogens at a high concentration and the adsorption capacity was determined from the residual concentration. Even after repeated regeneration and reuse, the adsorption capacity showed no substantial change.

Test Method

1. Determination of Adsorption Capacity

| | |
|---|---|
| Pyrogen solution: | 5 ml of aqueous solution of *E. coli* 0111:B4 (100 $\mu$g/ml). *soluble in phosphate buffer (pH 7, $\mu$ = 0.02). |
| PS-CA: | 0.5 g (wet). |
| Treatment time: | 1 hr. |

2. Regeneration Method

1. After the completion of the adsorption test, the PS-CA was immersed in 15 ml of a regeneration liquid (aqueous alkali/ethanol solution) for 12 hours.
2. Filtering through a microfilter (0.22 $\mu$m).
3. Washing with pyrogen-free water (30 ml ×5).
4. Washing with 1.5M aqueous solution of NaCl (30 ml ×5).
5. Washing with pyrogen-free water (30 ml ×5).

Results

| | Pyrogen concn. ($\mu$g/ml) test soln. | Pyrogen concn. ($\mu$g/ml) treated soln. | Adsorption capacity ($\mu$g/g wet) |
|---|---|---|---|
| after 1st run | 100 | 21 | 790 |
| after 2nd run | 100 | 8.8 | 910 |
| after 3rd run | 100 | 5.9 | 940 |

We claim:

1. A method for separating a phosphopolyol compound from its solution, comprising the steps of bringing the solution into contact with a porous adsorbent which has a pore size of 1 nm to 20 microns and comprises a base material and a functional chain group of an aliphatic amine having a chain length of 2 to 50, bonded to the base material through an ether bond.

2. The method as claimed in claim 1, in which the functional chain group is a primary or a secondary aliphatic amine group.

3. The method as claimed in claim 1, in which the adsorbent is in the form of hard gel beads having a pore size of 10 nm to 5 microns.

4. The method as claimed in claim 1, in which the adsorbent is in the form of a microfiltration membrane or an ultrafiltration membrane.

5. The method as claimed in claim 1, in which the phosphopolyol is a pyrogen and the solution is an aqueous solution of a drug or medicine having an ionic strength of from 0.03 to 0.5.

6. The method as claimed in claim 1, in which the phosphopolyol and a drug or medicine are adsorbed on the adsorbent and then the adsorbent is brought into contact with an aqueous solution having a high ionic strength to thereby elute the drug or medicine selectively.

7. A separating agent comprising a base material and a functional chain group having a chain length of 2 to 50 bonded to the base material through an ether bond, the functional chain group being an aliphatic primary or secondary amine group and said separating agent having a pore size of 1 nm to 20 microns.

8. The separating agent as claimed in claim 7, in which the functional chain group has a diaminoalkylene moiety of 1 to 12 carbon atoms.

9. The separating agent as claimed in claim 7, in which the base material is a polysaccharide or a polyvinyl alcohol polymer and has an intermediate group of a hydroxy-substituted propylene bonded to an oxygen atom of the base material.

10. The separating agent as claimed in claim 7, in which the functional chain group includes an amino acid residue bonded to the diaminoalkylene moiety.

11. The separating agent as claimed in claim 7, in which the base material is selected from the group consisting of a polysaccharide and a polymer of vinyl alcohol, the functional chain group includes a hydroxypropylene group bonded at its one end to an oxygen atom contained in the base material and the functional chain group is an aliphatic amine group having a chain length of 2 to 50.

12. The separating agent as claimed in claim 11, in which the functional group has a chain length of 3 to 35 and includes therein 1 to 5 nitrogen atoms.

13. The separating agent as claimed in claim 7, in which the base material is a porous polysaccharide and the functional group has the following formula:

$$\text{—(hydroxypropylene group)—}(NH(CH_2)_n)_m\text{—}B$$

in which n is a number of 1 to 12, m is zero or one and B is guanidino or a natural polyamine.

14. The separating agent as claimed in claim 7, in which the base material is a porous cellulose and the functional group has the following formula:

$$\text{—(hydroxypropylene group)—}(NH(CH_2)_6)\text{—guanidino.}$$

15. The separating agent as claimed in claim 7, in which the base material is a porous cellulose and the functional group has the following formula:

$$\text{—(hydroxypropylene group)—guanidino.}$$

16. The separating agent as claimed in claim 7, in which the base material is a porous polysaccharide and the functional group has the following formula:

$$—(CH_2—CH(OH)—CH_2)—(NH(CH_2)_n)_m—B$$

in which n is a number of 1 to 12, m is zero or one and B is guanidino or a natural polyamine.

17. A method of separating a phosphopolyol compound from its solution, comprising the steps of bringing the solution into contact with a porous adsorbent which comprises a polyhydroxyl polymer base material with a pore size of 50 nm to 1 micron having a functional chain group of an aliphatic amine having a chain length of 2 to 50 bonded thereto through an ether bond.

18. A separating agent comprising a polyhydroxyl polymer base material with a pore size of 50 nm to 1 micron having a functional chain group of an aliphatic amine having a chain length of 2 to 50 bonded thereto through an ether bond.

* * * * *